US 11,804,068 B2

United States Patent
Li

(10) Patent No.: US 11,804,068 B2
(45) Date of Patent: Oct. 31, 2023

(54) SYSTEMS AND METHODS FOR IMAGE FEATURE RECOGNITION USING A LENSLESS CAMERA

(71) Applicant: Rovi Guides, Inc., San Jose, CA (US)

(72) Inventor: Zhu Li, Overland Park, KS (US)

(73) Assignee: Rovi Guides, Inc., San Jose, CA (US)

( * ) Notice: Subject to any disclaimer, the term of this patent is extended or adjusted under 35 U.S.C. 154(b) by 17 days.

(21) Appl. No.: 17/712,325

(22) Filed: Apr. 4, 2022

(65) Prior Publication Data
US 2023/0316804 A1   Oct. 5, 2023

(51) Int. Cl.
| | |
|---|---|
| *G06V 40/16* | (2022.01) |
| *A61B 5/1171* | (2016.01) |
| *A61B 5/00* | (2006.01) |
| *G06F 21/32* | (2013.01) |
| *G06V 10/42* | (2022.01) |
| *G06V 10/77* | (2022.01) |

(52) U.S. Cl.
CPC .......... *G06V 40/164* (2022.01); *A61B 5/1176* (2013.01); *A61B 5/7253* (2013.01); *G06F 21/32* (2013.01); *G06V 10/431* (2022.01); *G06V 10/7715* (2022.01); *G06V 40/166* (2022.01); *G06V 40/169* (2022.01); *G06V 40/172* (2022.01)

(58) Field of Classification Search
CPC .............. G06V 40/164; G06V 10/431; G06V 10/7715; G06V 10/166; G06V 10/169; G06V 10/172; A61B 5/1176; A61B 5/7253; G06F 21/32
See application file for complete search history.

(56) References Cited

U.S. PATENT DOCUMENTS

| | | | |
|---|---|---|---|
| 11,386,349 B1* | 7/2022 | Prisadnikov | G06N 20/00 |
| 11,651,020 B2* | 5/2023 | Bonfield | G06F 16/24578 |
| | | | 707/734 |
| 2019/0347388 A1* | 11/2019 | Jiang | G06V 10/82 |
| 2020/0397336 A1* | 12/2020 | Sherry | G06T 5/10 |
| 2022/0116513 A1* | 4/2022 | Kellermann | H04N 1/4493 |
| 2022/0132052 A1* | 4/2022 | Mojaver | A61B 5/4875 |

(Continued)

OTHER PUBLICATIONS

Zheng et al., A Simple Framework for 3D Lensless Imaging with Programmable Masks, 2021.*

(Continued)

*Primary Examiner* — John B Strege
(74) *Attorney, Agent, or Firm* — Haley Guiliano LLP

(57) ABSTRACT

Systems and methods are described for generating pixel image data, using a lensless camera, based on light that travels through a mask that with pattern masking the lensless camera. The system applies a transformation function to the pixel image data to generate frequency domain image data. The system inputs the frequency domain image data into a machine learning model, wherein the machine learning model does not have access to data that represents the pattern of the mask. The model is trained using a set of images with the feature that are captured by the flat, lensless camera through the mask. The system processes the frequency domain image data using the machine learning model to determine whether the pixel image data depicts the image feature. The system further performs an action based on determining that the pixel image data depicts the image feature.

20 Claims, 10 Drawing Sheets

(56) References Cited

U.S. PATENT DOCUMENTS

2022/0198824 A1\* 6/2022 Niaf .................. G06V 40/1359
2023/0153604 A1\* 5/2023 Byeon .................... G06F 30/27
                                                         706/15

OTHER PUBLICATIONS

Asif et al., "FlatCam: Thin, Lensless Cameras Using Coded Aperture and Computation," in IEEE Transactions on Computational Imaging, vol. 3, No. 3, pp. 384-397, Sep. 2017.
Khan et al., "FlatNet: TowardsPhotorealistic Scene Reconstruction from Lensless Measurements," IEEE T-PAMI, pp. 1-22, 2020.
Gonzalez et al., "Digital Image Processing (3rd Edition)", Pearson (2007).
Tan et al., "Face Detection and Verification Using Lensless Cameras," in IEEE Transactions on Computational Imaging, vol. 5, No. 2, pp. 180-194, Jun. 2019.

\* cited by examiner

Mask Partially Masks the Sensor

Position Mask Over Sensor

SYSTEMS AND METHODS FOR IMAGE FEATURE RECOGNITION USING A LENSLESS CAMERA

BACKGROUND

This disclosure is directed to systems and methods for using a lensless camera that is distorted by a mask with a private pattern and/or a private sensor field that masks the lensless camera. More particularly, systems and methods are provided for detecting features in a heavily distorted image captured by the lensless camera without knowledge of the private pattern and/or sensor field and without an ability to reconstruct an undistorted image.

SUMMARY

Advancements in video camera and computerized video processing technology have enabled expanded use of video cameras as action sensors in addition to their use as simple video capture devices. For example, detection of the presence of a certain person, as captured by a camera, can trigger a variety of actions such as logging a user in to an application, unlocking a device, personalizing a media experience, etc. However, installation of cameras can present a serious privacy risk to content consumers and potential legal liability for content providers. For example, users may be reluctant to install cameras in their homes out of fear of sacrificing their privacy. In fact, many users resort to covering up their cameras with paper or tape because of privacy concerns. A choice to not install a camera, or to cover up a camera, however, can significantly reduce the ability of a device to perform one or more of its capabilities according to its full functionality (e.g., a user may need to log in by manually entering a password instead of using a face-recognition camera-enabled login functionality).

To help address these issues, systems and methods are provided herein that enable a computer device to perform feature detection in a heavily distorted image captured by a masked camera (e.g., detecting the presence of a particular person or human face) without providing unwanted computer devices with an ability to fully reconstruct a full, undistorted image. More particularly, a lensless camera-based imaging system is provided for image-feature recognition that offers strong privacy (e.g., preventing an ability to reconstruct the full, undistorted image). An algorithm is also provided herein to achieve high-accuracy image recognition using data captured by such a camera. The algorithm may be performed by a feature detection application executed by the computing system.

More particularly, the system may utilize a computing system that is communicatively connected to a lensless camera (e.g., a complementary metal-oxide-semiconductor (CMOS) sensor) for capturing an image of an environment (e.g., by converting detected photons into electric signals). The lensless camera may include a physical mask that comprises a predetermined pattern (e.g., a pinhole pattern). For example, the physical mask may comprise an opaque material with apertures (e.g., that allow light to pass through), where the apertures may be shaped according to the pattern. Alternatively, the pattern may refer to the pattern of the opaque material. The mask pattern may be generated using random spacing of opaque or clear bands and/or shapes, or created according to an obfuscated algorithm, or manually created by a provider or by a user. The pattern of the mask may distort (e.g., blur) the captured image data, for example by casting a shadow on the light-sensing part of the camera and/or by causing refraction in the incoming light.

In a normal mode of operation, the computing system does not have access to data that represents the pattern of the mask. Because the camera is lensless and does not focus the incoming light, it is mathematically impossible for the computing system to reconstruct the distorted image of the environment based on light that passed through the pattern. An algorithm is further provided so the computing system may detect image features (e.g., presence of a certain human face) in the undistorted image using data from the masked lensless camera without fully recovering the undistorted image. In some embodiments, the pixel image data captured by the masked lensless camera is processed by an application of transformation function (e.g., a discrete cosine transform or fast Fourier transform) to generate frequency domain image data.

The frequency domain image data may then be input into a machine learning model. In particular, the machine learning model may be trained using a set of images known to contain the feature (e.g., images captured using the masked lensless camera). The machine learning model processes the frequency domain image data to determine whether the image feature is present in the pixel image data (e.g., if the pixel image data was decoded using the pattern data). The computing system may then perform an action based on the determination that the pixel image data depicts the image feature (e.g., depicts a face of a particular user). The action may be, for example, unlocking an application, authorizing a transaction, allowing access to a device, controlling playback of a media asset (e.g., by inserting personalized content), or any other suitable action.

In some aspects of this disclosure, the machine learning model may use, as an input, frequency domain image data that was divided into a plurality of frequency bands. For example, the plurality of bands may comprise a band comprising direct current (DC) component and low-frequency alternating current (AC) components of the frequency domain image data; a band comprising a horizontal frequency portion of the frequency domain image data; a band comprising a vertical frequency portion of the frequency domain image data; and/or a band comprising a high-frequency diagonal portion of the frequency domain image data. In some embodiments, any number of frequency bands may be used.

Each band may be separately input into at least one convolution layer of the machine learning model. Each output of the at least one convolution layers may be used to generate an attention map for each band data. The attention maps may then be concatenated, and the concatenated data may be passed through additional convolution layers. The result of passing the data through the additional convolution layers may be used to generate an additional attention map. The additional attention map may be input into at least one fully connected layer of the machine learning model. The output of the at least one fully connected layer of the machine learning model may be used to [missing word?] computer probability of an image feature presence (e.g., using a softmax function).

As a result of the use of the masked lensless camera and the use of the trained machine learning model, the computing device can detect a presence of an image feature (e.g., face of the user) without being able to or needing to (fully) reconstruct the image. This allows the ability to place such cameras in any location without concerns of compromising security or privacy by, e.g., capturing images able to be viewed by a human. In one approach, the user may provide the private pattern data to the computing system (e.g., by attaching a dongle storing this private pattern data) to allow the computing device to reconstruct the image (e.g., while the dongle is attached).

BRIEF DESCRIPTION OF THE DRAWINGS

The present disclosure, in accordance with one or more various embodiments, is described in detail with reference to the following figures. The drawings are provided for purposes of illustration only and merely depict typical or example embodiments. These drawings are provided to facilitate an understanding of the concepts disclosed herein and should not be considered limiting of the breadth, scope, or applicability of these concepts. It should be noted that for clarity and ease of illustration, these drawings are not necessarily made to scale.

DETAILED DESCRIPTION

Figure 1B:
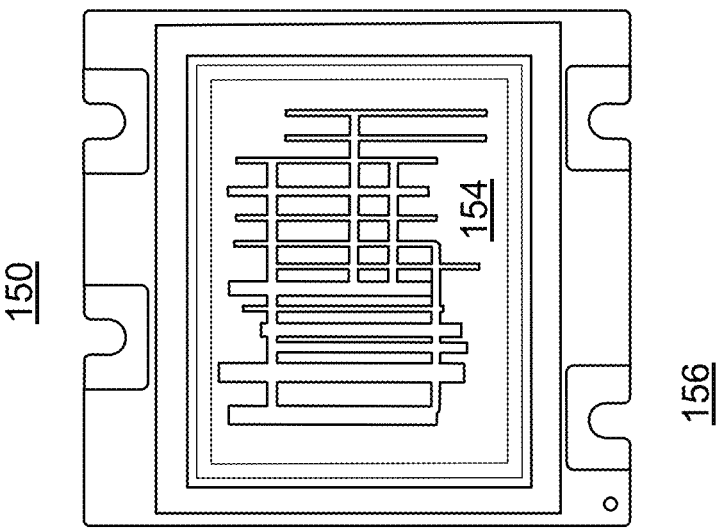
FIG. 1B shows a view of an example assembly of a lensless camera and a mask, in accordance with some embodiments of this disclosure.
Figure 1A:
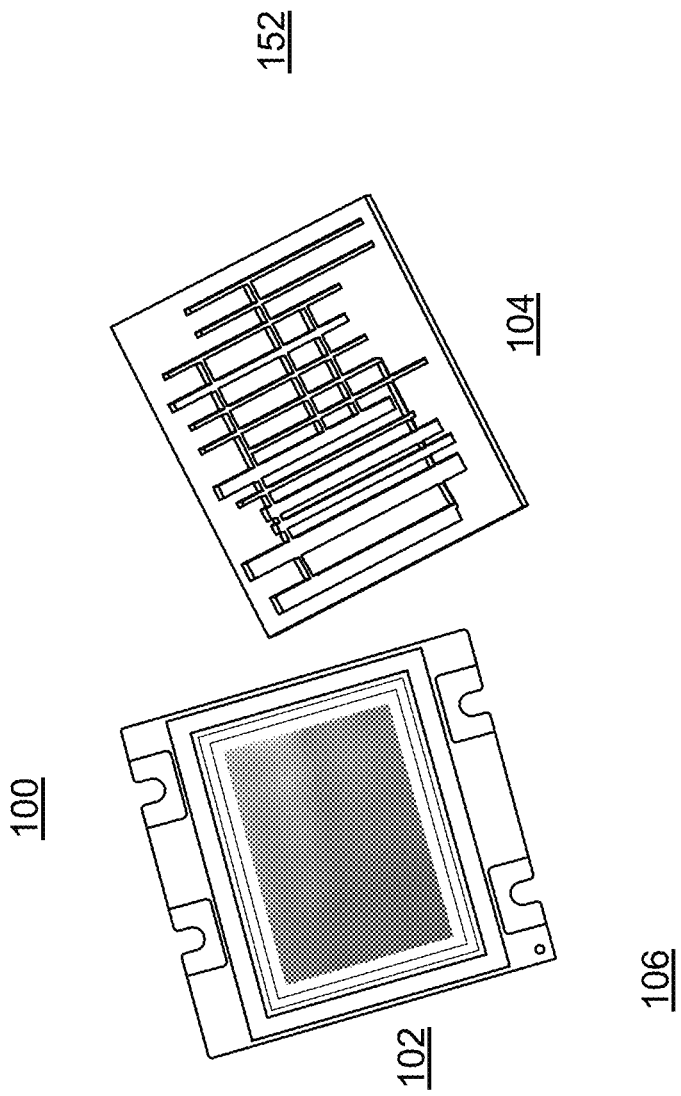
FIG. 1A shows a view of an example lensless camera and a mask, in accordance with some embodiments of this disclosure.

FIG. 1A shows view 100 of a lensless camera 102 and mask 104, in accordance with some embodiments of this disclosure. Lensless camera 102 may be a CMOS sensor, a charge-coupled device (CCD) sensor or any other suitable type of a light sensor configured to produce pixel data that is based on light hitting a light-sensitive front of the lensless camera 102.

Mask 104 may be manufactured out of any suitable opaque material that prevents penetration by light. For example, mask 104 may be manufactured using plastic, metal, wood, (stained) glass or any other suitable opaque materials. In some embodiments, mask 104 may comprise one or more apertures forming a pattern. The apertures may allow penetration of light to camera 102. The aperture pattern may be defined randomly. For example, the aperture pattern may be selected by selecting randomly spaced horizontal and vertical cuts of randomly selected length and width. In another example, a certain number of randomly positioned and/or shaped holes may be selected. The pattern may also be created using a hidden algorithm, the algorithm not accessible to anyone trying to decode the pattern. The pattern may also be selected by a manufacturer or by the end user. For example, the user may be able to define any kind of pattern and 3D-print mask 104 with the defined pattern. The term "pattern" may refer to the configuration of the opaque material of mask 104 or the configuration of the apertures of mask 104. In some embodiments, the apertures of mask 104 may be filled with transparent material (e.g., glass or clear plastic). In some embodiments, mask 104 may be a transparent material (e.g., glass or clear plastic) with a pattern of opaque markings printed on the transparent material. During the manufacturing process, or in post-production, mask 104 may be positioned 106 over camera 102. In some embodiments, mask 104 may be sold or provided separately from camera 102 and positioned 106 over camera 102 by an end user or installation technician.

FIG. 1B shows a view of an assembly of a lensless camera 152 and mask 154, in accordance with some embodiments of this disclosure. For example, camera 152 may be the same as camera 102 and mask 154 may be the same as mask 104. Once assembled, mask 152 may block or refract 156 some light coming to camera 152, e.g., such that sensor of camera 152 (e.g., CMOS sensor, CCD sensor, etc.) is able to receive light only through the apertures in mask 154 to form heavily distorted (e.g., blurred) image data. As will be explained, an undistorted image is not recoverable based on pixel data produced by camera 152 without data that defines at least the dimensions of the pattern of mask 154. In some embodiments, additional data that defines the properties of the mask may be needed (e.g., sensor field of the mask).

Figure 2A:
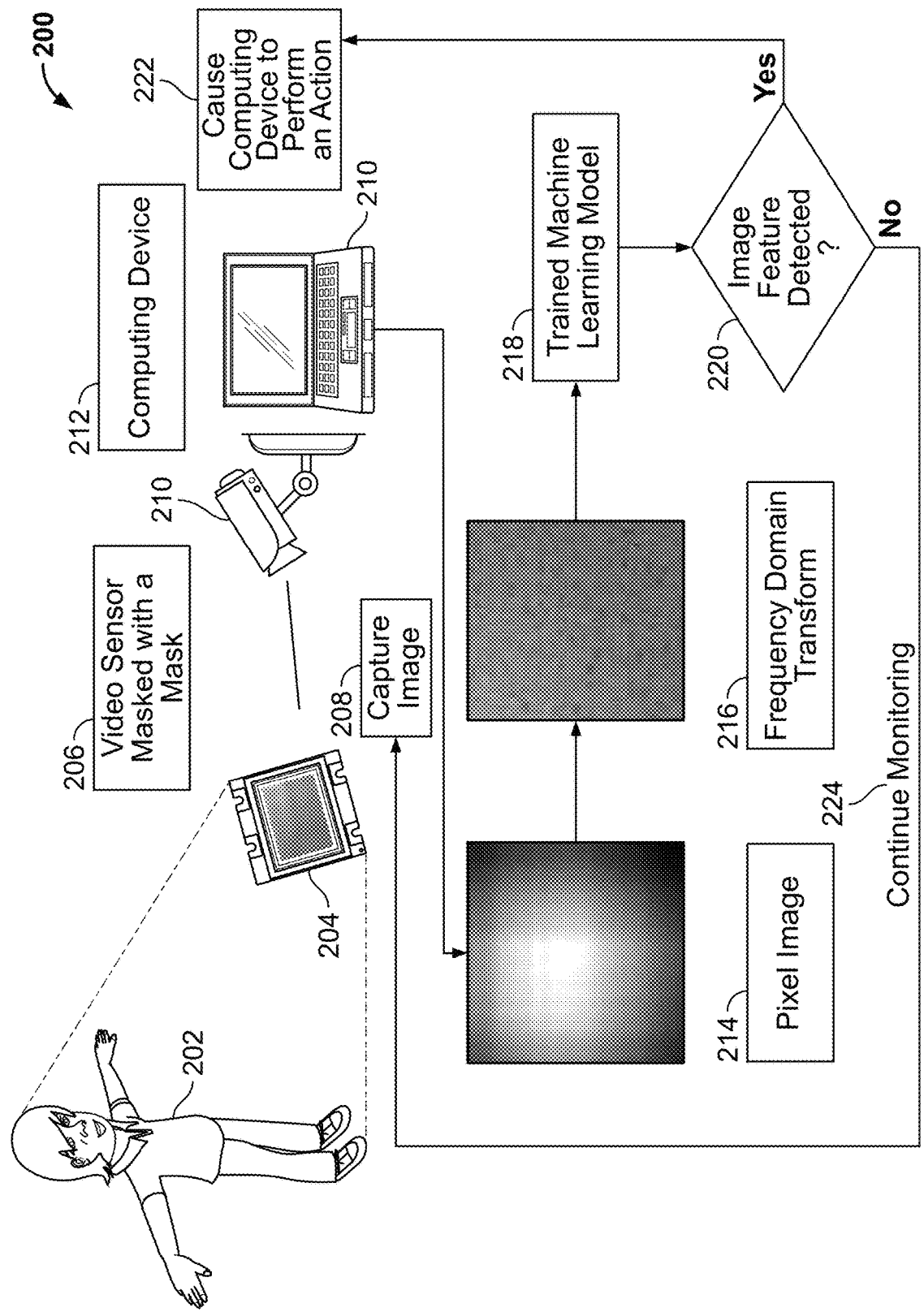
FIG. 2A shows an illustrative technique for image feature detection, in accordance with some embodiments of this disclosure.

FIG. 2A shows an illustrative technique 200 for image feature detection, in accordance with some embodiments of this disclosure. In particular, computing device 212 may be used to detect a presence of a feature (e.g., recognize a face of a certain user) in an undistorted version of an image captured 208 by camera 210. Computing device 212 may be any suitable type of a computing device, including a personal computer, a laptop, a smartphone, tablet, set-top box, an embedded circuit, a system on a chip, or any other suitable computing device, or any combination thereof. In some embodiments, steps described below may be performed by a feature detection application executed by computing device 212 (e.g., based on instruction stored in non-volatile memory of device 212).

In some embodiments, computing device 212 may include camera 210 or be in communicative connection with camera 210. Camera 210 may include video sensor 204 (e.g., a flat, lensless light sensor) masked 206 by a mask with a certain aperture pattern. Flat, lensless cameras are described in more detail in M. S. Asif, A. Ayremlou, A. Sankaranarayanan, A. Veeraraghavan and R. G. Baraniuk, "FlatCam: Thin, Lensless Cameras Using Coded Aperture and Computation," in IEEE Transactions on Computational Imaging, vol. 3, no. 3, pp. 384-397, September 2017, which is hereby incorporated by reference herein in its entirety. For example, mask 104 shown in FIG. 1A may be used as mask 206. Camera 210 may be configured to capture image 202 (e.g., of a physical environment including a person 202 facing the camera). For example, flat camera 204 may detect light passing through the pattern of the mask to generate an electrical signal, which is then converted by circuitry of camera 210 and/or circuitry of computing device 212 to a pixel image data 214. As shown, pixel image data 214 is affected by noise introduced by the mask and, therefore, appears distorted (e.g., heavily blurred). An image of a user and/or a user's face in pixel image data 214 is unrecognizable to the naked eye or to typical vision algorithms. As will be explained below (e.g., in relation to FIG. 3), the undistorted version of the pixel data may be generated by a computing device that has access to data that defines the shape of the pattern of the mask that masks sensor 204. However, without access to such pattern definition data, a computing device cannot recover the undistorted version of pixel image data 214. Still, data captured in pixel image data 214 may include image features, unrecognizable by humans, that may be detected by a model and used to trigger events.

Computing device 212 may perform a frequency domain transformation of the pixel image data 214 to produce frequency domain image data 216. In some embodiments, the frequency domain transformation may comprise a discrete cosign transformation (DST), a fast Fourier transformation (FFT), integral wavelet transforms, or any kind of other suitable frequency domain transformation. Computing device 212 may then input the frequency domain image data into a trained machine learning model 218 configured on the computing device 212 (or another remote device that is communicatively coupled to computing device 212). In some embodiments, frequency domain image data may be split into several bands, and each of the bands may be processed by a trained machine learning model 218 separately using one or more convolution layers of the machine learning model. An attention map may be generated for each band, before the band data is combined. The combined data may be fed through an additional convolution layer of trained machine learning model 218. The output of the additional convolution layer of the trained machine learning model 218 may be used to create another attention map. The attention map may then be used as an input for or more fully connected layers of the trained machine learning model 218. The output of the one or more fully connected layers of the trained machine learning model 218 may be used to compute a probability that the (inaccessible) undistorted version of the pixel data includes an image feature (e.g., presence of a face of a certain user). Full functionality of example machine learning model 218 is described in more detail below in relation to FIG. 4.

Machine learning model 218 may be trained using a training set of images captured by camera 210 that are known to include the features to be detected (e.g., a face of a user). More particularly, training of machine learning model 218 using pixel data captured by masked camera 206 may comprise training machine learning model 218 to detect features in the image without the need for separately input data that defines the dimensions of the private/secret pattern. Example techniques for training of the machine learning model 218 are describe below with respect to FIG. 2B.

If the feature is not detected by trained machine learning model 218, e.g., the calculated probability the feature is present is determined to be below a threshold, computing device 212 may capture a next image 224 using camera 210 and repeat the monitoring process. If the feature is detected by trained machine learning model 218, computing device 212 may perform an action based on the feature. For example, computing device 212 may become unlocked for the user 202, grant access to a specific application to user 202, or play media content relevant to user 202. Other example features and actions based on features are discussed below in relation to FIG. 8.

Figure 2B:
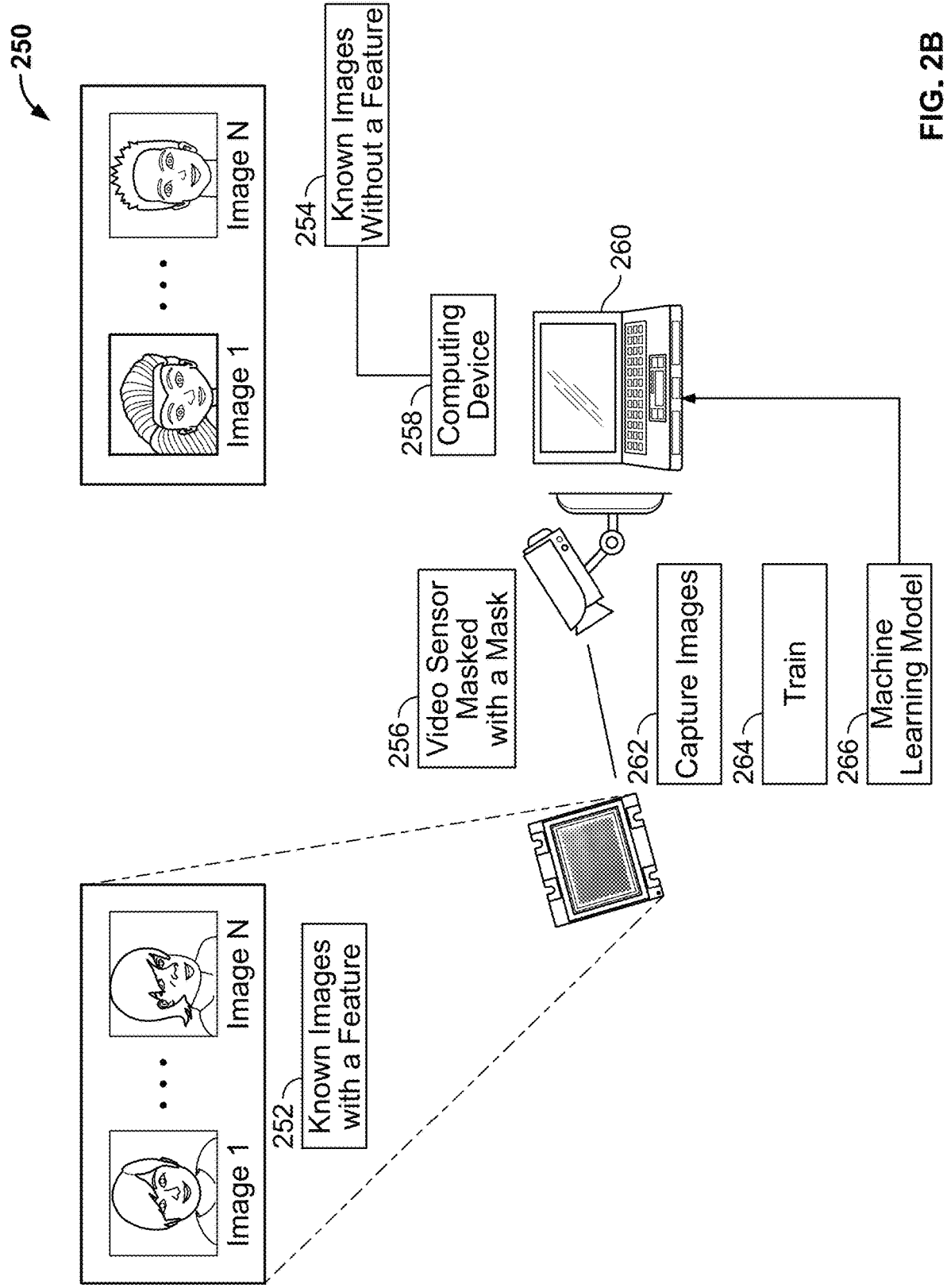
FIG. 2B shows an illustrative technique for training a machine learning model for image feature detection, in accordance with some embodiments of this disclosure.

FIG. 2B shows an illustrative technique 250 for training a machine learning model 266 (which may be the same as machine learning model 218 of FIG. 2A) for image feature detection, in accordance with some embodiments of this disclosure. For example, techniques 250 may be applied to train machine learning model 218 of FIG. 2A.

More particularly, a computing device may be trained using a set of images 252 known to include a depiction of a particular image feature (e.g., face of a certain person). Image set 252 may be acquired by computing device 260, for example, by requesting that a user pose for camera 258 from several different angles to capture 262 the set of images 252. In particular, the images are acquired by a sensor masked by a mask 256 (e.g., mask 104 of FIG. 1A). In some embodiments, image set 252 may comprise photographs of a user the system is being trained to detect, where the photos are different angles of the user (and/or the user's face). For example, a user may be asked to pose looking straight at the camera to acquire image 1 of image set 252. In another example, the user may be asked to pose looking at the camera sideways to acquire image N of image set 252. Any other suitable method of acquiring image set 252 may be used. For example, if the desired image feature to detect is a user holding their arms out to the sides (e.g., as shown in element 202 of FIG. 2A), the set of images may be created by using known stock images of humans in that pose. For instance, such training photographs may be displayed at a proper distance to be captured via camera 258 (using a sensor masked by mask 256).

Additionally (as an option), a set of images 254 known not to depict the desired feature to detect may also be acquired for training purposes. For example, computing device 260 may prompt the user to hold up several pre-printed images of random people for camera 258. In this way, a sensor masked by a mask 256 will capture a set of images known not to include the face of the user. Any other suitable method of acquiring such a set of images 254 may be used.

Images from image set 252 may be used to train 264 machine learning model 266. For example, in a forward phase of training, image 1 of image set 252 may be input into untrained or partially trained machine learning model 266, to acquire an output that attempts to determine whether the image 1 of set 252 includes the desired image feature. The success or failure of output may be used to perform a backward phase to modify weights and coefficients assigned to any convolution layers, attention map, or fully connected layers of machine learning model 266. For example, success may be used to reinforce or fine tune the weights and/or coefficients, while failure may lead to larger changes of the coefficients. If the machine learning model 266 includes layers for generation of attention maps, the coefficients for the attention map gemmation layers may be trained in the same fashion. Each image of image set 252 and image set 254 may be input through the machine learning model 266, one or more times during the training process, e.g., to repeat forward and backward training phases using different inputs of the training until performance stops improving.

Figure 3:
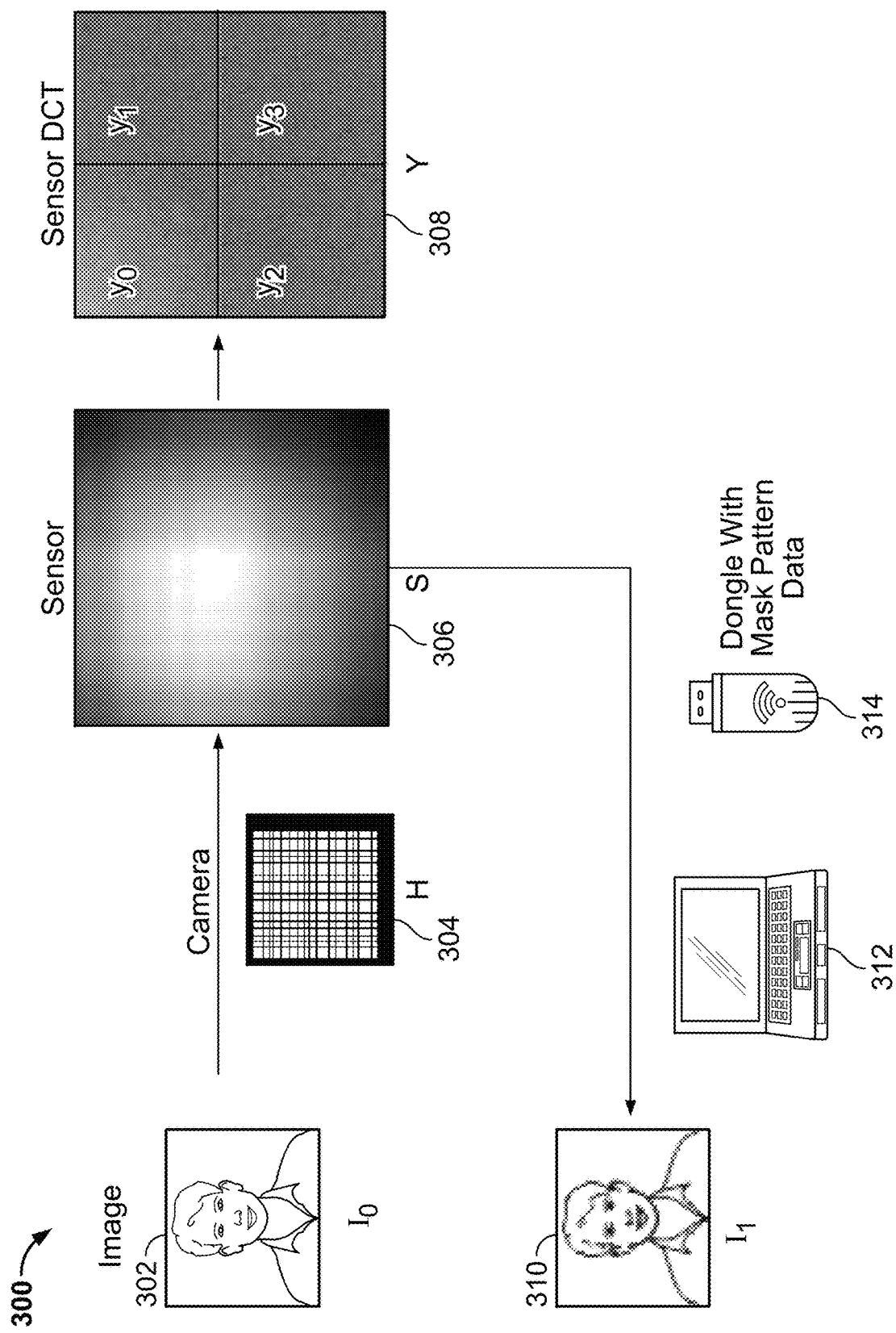
FIG. 3 shows an illustrative technique for processing image pixel data, in accordance with some embodiments of this disclosure.

FIG. 3 shows an illustrative technique for processing image pixel data, in accordance with some embodiments of this disclosure. For example, the shown technique may be used by computing device 312 (which may be the same as device 212 of FIG. 2A) to process image pixel data captured by camera 210 (of FIG. 2A).

In one approach, unsourced image 302, labeled $I_0$ (where $I_0$ is a pixel matrix), is received by a camera (e.g., by camera 210 of FIG. 2A) that includes a flat light sensor and a mask (e.g., as shown by elements 152 and 154 of FIG. 1). The pattern of mask 304 may be defined by matrix H (e.g., where 0s represent transparent portions and 1s represent opaque portions or where 1s represent transparent portions and 0s represent opaque portions). The masked pixel image data 306 generated by the camera may be represented by a pixel matrix S. As shown, pixel matrix S appears completely dissimilar to image $I_0$ and image $I_0$ is not recoverable from matrix S without pattern data matrix H.

In some embodiments, computing device 312 may further process the pixel matrix S by applying a frequency domain transform to the pixel matrix S (306) to acquire frequency domain data Y (308). For example, the frequency domain transform may be a discrete cosign transform. The frequency domain data Y may be divided into a plurality of frequency bands. While four bands ($Y_0$, $Y_1$, $Y_2$, and $Y_3$) are shown, any number of bands may be used. In some embodiments, $Y_1$ may be a band comprising a direct current (DC) component and low-frequency alternating current (AC) components of the frequency domain image data; $Y_2$ may be a band comprising a horizontal frequency portion of the frequency domain image data; $Y_3$ may be a band comprising a vertical frequency portion of the frequency domain image data; and $Y_4$ may be a band comprising a high-frequency diagonal portion of the frequency domain image data.

In one approach, the plurality of bands (e.g., $Y_0$, $Y_1$, $Y_2$, and $Y_3$) may be input into a machine learning model (e.g., model 218 of FIG. 2A). The operation of the machine learning model to identify the presence of an image feature in image $I_0$ without fully recovering the image $I_0$ is described below in more detail in relation to FIG. 4.

In some embodiments, computing device 312 may recover a version of image $I_0$ as pixel matrix $I_1$ if it gains access to data matrix H. For example, a user may plug a dongle 314 into device 312 where the dongle stores data matrix H, e.g., as a key to decode and recover an image. In this example, computing device 312 may acquire pixel matrix $I_1$ which is similar to image $I_0$. This recovery may be performed by a convolution system with masks determined by the mask pattern stored as data matrix H. The images can then be reconstructed from the sensor measurement by a Wiener filtering. Wiener filtering is further described in Lim, Jae S. "Two-dimensional signal and image processing," Englewood Cliffs (1990), which is hereby incorporated by reference herein in its entirety.

For example, if the image scene $I_0(x, y)$ is N×N pixels, while the mask is H(x, y) of M×M elements, then computing device 312 may compute a measurement S(x, y) of (N+M−1)×(N+M−1) elements as follows:

$$S = (I_0 + n_0) \times H$$

The reconstructed images may be obtained by computing device 312 performing an inverse filter of the measurement to obtain the input image. Wiener filter is the optimal solution for this, which is computed in the frequency domain via a Wiener kernel given as:

$$W(u, v) = \frac{H^*(u, v)}{|H(u, v)|^2 + \frac{P_n(u, v)}{P_1(u, v)}}$$

where H(u,v) is the FFT of mask H, $P_1(u,v)$ is the power spectrum of input image $I_0$, while $P_n(u,v)$ is the power spectrum of the noise $n_0$. Computing device 312 may then acquire a reconstructed image $I_1$ as the inverse FFT of the Wiener filtered measurement:

$$I_1 = iFFT(S(u,v) \times W(u,v))$$

Thus, with the full knowledge of the lensless camera mask (e.g., from dongle 314) H(x,y), and knowledge of the signal to noise ratio (SNR) of the power spectrum of the image vs. the noise, a reconstruction $I_1$ can be achieved. But when this mask information H is kept as private/secret information, then even with the measurement, it is impossible to reconstruct pixels from the measurement, and hence the strong privacy protection is achieved. Image recognition may be performed using reconstructed images (using the pattern data), e.g., as also described in S. S. Khan, V. Sundar, V. Boominathan, A. Veeraraghavan, and K. Mitra, "FlatNet: Towards Photorealistic Scene Reconstruction from Lensless Measurements," IEEE T-PAMI, 2020, and J. Tan et al., "Face Detection and Verification Using Lensless Cameras," in IEEE Transactions on Computational Imaging, vol. 5, no. 2, pp. 180-194, June 2019, both of which are hereby incorporated by reference herein in their entirety. In some embodiments, sensor field data may be needed in addition to data H to reconstruct the image $I_1$.

Figure 4:
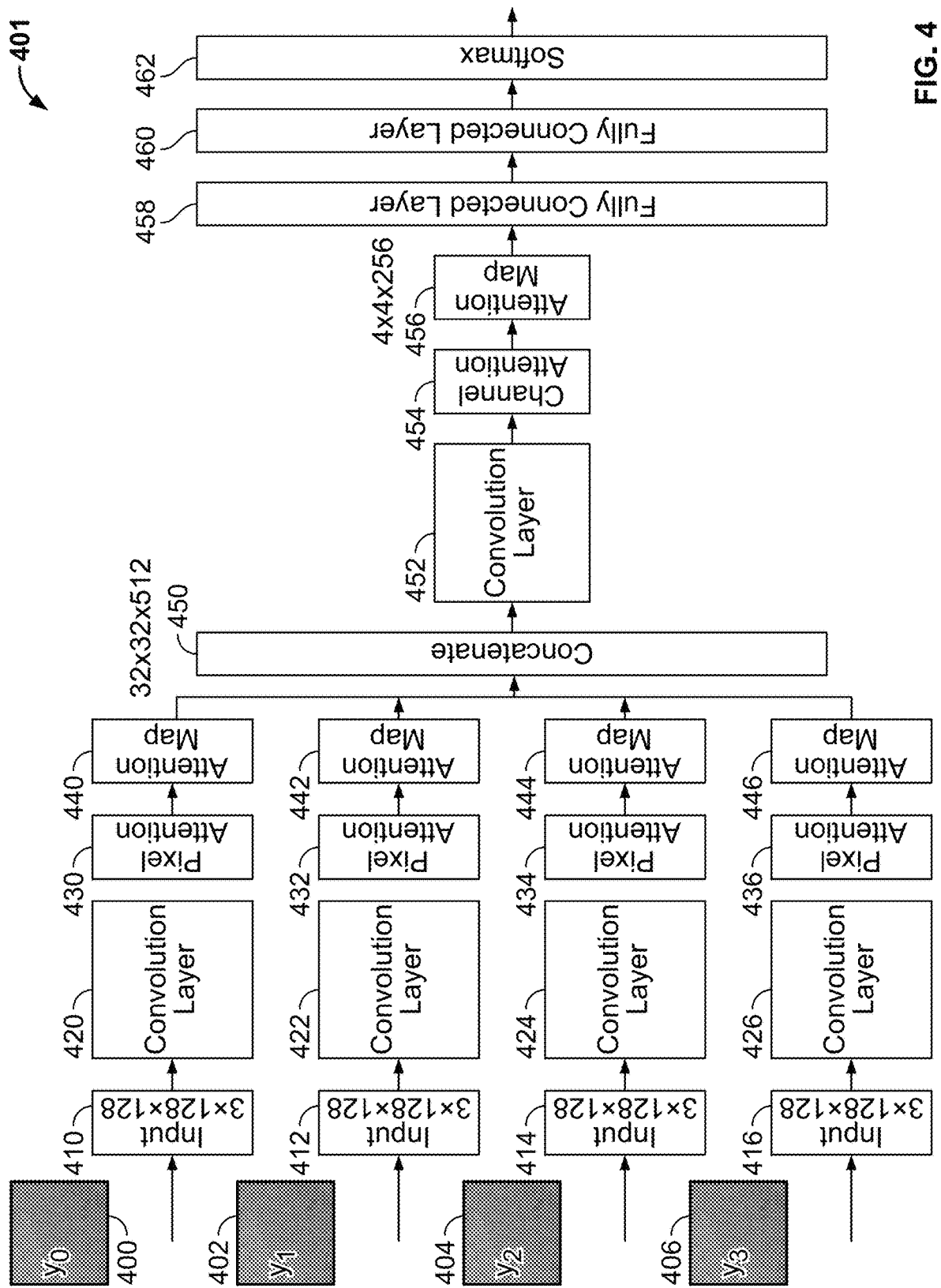
FIG. 4 shows an illustrative block diagram of an example machine learning model, in accordance with some embodiments of this disclosure.

FIG. 4 shows an illustrative block diagram of an example machine learning model 401, in accordance with some embodiments of this disclosure. Machine learning model 401 may be implemented as software, hardware, or a combination of the above on any suitable computing device (e.g., on computing device 212) or any suitable combination of suitable computing devices. For example, machine learning model 401 may be software executed by computing device 212 or by a remote device (e.g., a cloud computing device) communicatively connected to computing device 212.

In some embodiments, machine learning model 401 may take as inputs, e.g., bands of frequency domain data 308 of FIG. 3. For example, machine learning model 401 may include multiple pathways for separately processing a plurality of bands of frequency domain data. While four different pathways for the machine learning model are shown as part of machine learning model 401, any number of pathways may be employed. For example, if frequency domain data is divided into 16 sets of bands, 16 pathways may be used instead of four. In particular, separate processing of the bands mitigates problems of slow receptive field size growing in a typical pixel domain deep learning network.

As shown in illustrative example, machine learning model 401 operates on frequency domain data (e.g., discreet cosine transform data) divided into four bands 400, 402, 404, and 406. In some embodiments, band 400 may be a band comprising a direct current (DC) component and low-frequency alternating current (AC) components of the frequency domain image data; band 402 may be a band comprising a horizontal frequency portion of the frequency domain image data; band 404 may be a band comprising a vertical frequency portion of the frequency domain image data; and band 404 may be a band comprising a high-frequency diagonal portion of the frequency domain image data. In one example, each band may be a matrix input data with 3×128×128 dimensionality (however, other suitable input dimensionalities may also be used). For example, each of inputs 410, 412, 414, and 416 may be a 3×128×128 numerical matrix.

Each of the inputs 410, 412, 414, and 416 may be input into a respective set of convolution layers 420, 422, 424, 426 of a machine learning model 401. Each set of convolution layers 420, 422, 424, 426 may comprise one or more convolution layers. Each convolution layer may, for example, be a ResBlock convolution net. ResBlock portions may be implemented, e.g., as described in "Deep Residual Learning for Image Recognition," He et al., Computer Vision and Pattern Recognition, Dec. 10, 2015, which is hereby incorporated by reference herein in its entirety. In another example, each convolution layer may, for example, be a VGG convolution net, e.g., as described in "Very Deep Convolutional Networks for Large-Scale Image Recognition," Karen Simonyan, Sep. 4, 2014, Computer Vision and Pattern Recognition, which is herein incorporated by reference in its entirety.

Machine learning model 401 may separately apply respective pixel attention functions 430, 432, 434, 436 to output of convolution layer sets 420, 422, 424, 426 to generate respective attention maps 440, 442, 444, 446. Pixel attention may be performed as described by "Efficient Image Super-Resolution Using Pixel Attention," Hengyuan Zhao et al., Oct. 2, 2020, which is hereby incorporated by reference herein in its entirety. As a result of processing each band data by a set of convolution networks and by attention map function, the dimensionality of data may be reduced (e.g., each band data may now be a 32×32×128 matrix).

Machine learning model 401 may than concatenate 450 data from each pathway for processing band data. For example, four 32×32×128 matrices may be concatenated to create a single 32×32×512 matrix.

The single matrix can then be input into additional sets of convolution layers 452 (e.g., VGG or ResBlock convolution layers). The output of the additional set of convolution layers may be processed with a channel attention function 454 to generate attention map 456. Channel attention may be performed as describe by "ECA-Net: Efficient Channel Attention for Deep Convolutional Neural Networks," Wang et al., Oct. 8, 2019, which is hereby incorporated by reference herein in its entirety. As a result of processing each band data by an additional set of convolution networks and by channel map function, the dimensionality of data may be reduced (e.g., attention map 456 may be a matrix with 4×4×256 dimensions).

Attention map 456 may be further processed by a set of fully connected neural layers 458, 460. Fully connected layers are further described by Chellapilla, "High Performance Convolutional Neural Networks for Document Processing," Tenth International Workshop on Frontiers in Handwriting Recognition, Université de Rennes, Oct. 1, 2006, which is hereby incorporated by reference herein in its entirety. The output of the fully connected neural layers 458, 460 may then be used to directly estimate a likelihood of the initial image data depicting a certain image feature (for which machine learning model 401 was trained). For example, softmax function 462 may be applied to output of the fully connected neural layers 458, 460 to generate probabilities of initial image data depicting a certain image feature (e.g., a face of a particular user). In some embodiments, probability higher than 75% (or any other suitable threshold, e.g., 80%, 90% or 99%) may be interpreted as evidence that the initial image data is depicting a certain image feature, which may cause the computing device to perform a certain action (e.g., unlock the full functionality of the computing device, trigger a notification or an alarm, etc.).

Machine learning model 401 may have been trained as shown in FIG. 2B. For example, training sets of data (e.g., sets 252 and 254) may have been forward propagated through the machine learning model 401. After the forward propagation, back propagation may have occurred to adjust coefficients and weights of every layer of the machine learning model 401, including layers 420-426, 430-436, 452, 454, and 458-460 (e.g., weights and coefficients may have been modified for each convolution layer, each pixel attention layer, each channel attention layer, and each fully connected layer). In some examples, the softmax function 462 may also be adjusted during the training of machine learning model 401 (e.g., training the model with images captured by a masked camera that are known to depict a certain image feature, such as a face of particular user).

Figure 5:
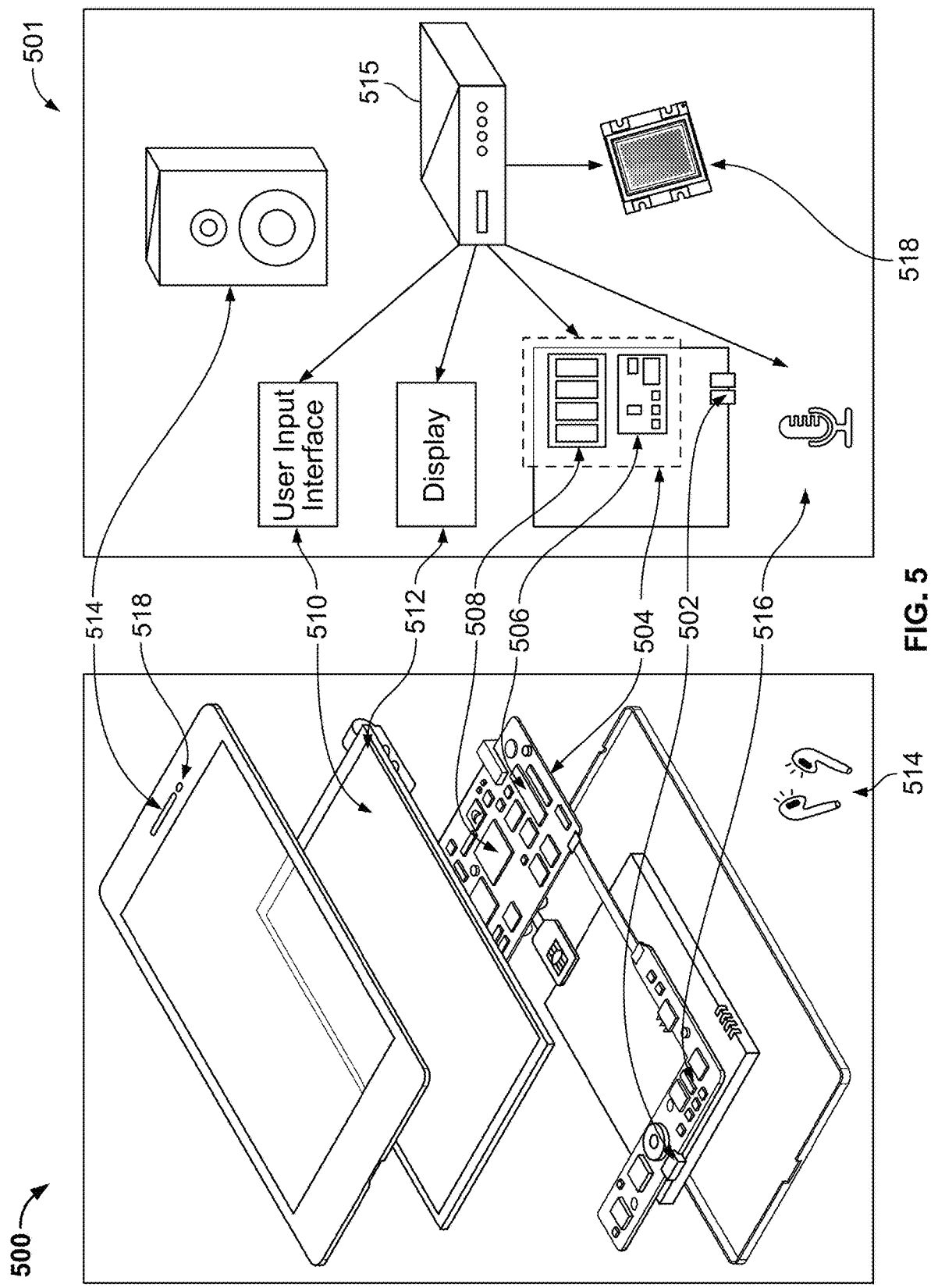
FIG. 5 shows an illustrative user equipment device, in accordance with some embodiments of this disclosure.
Figure 6:
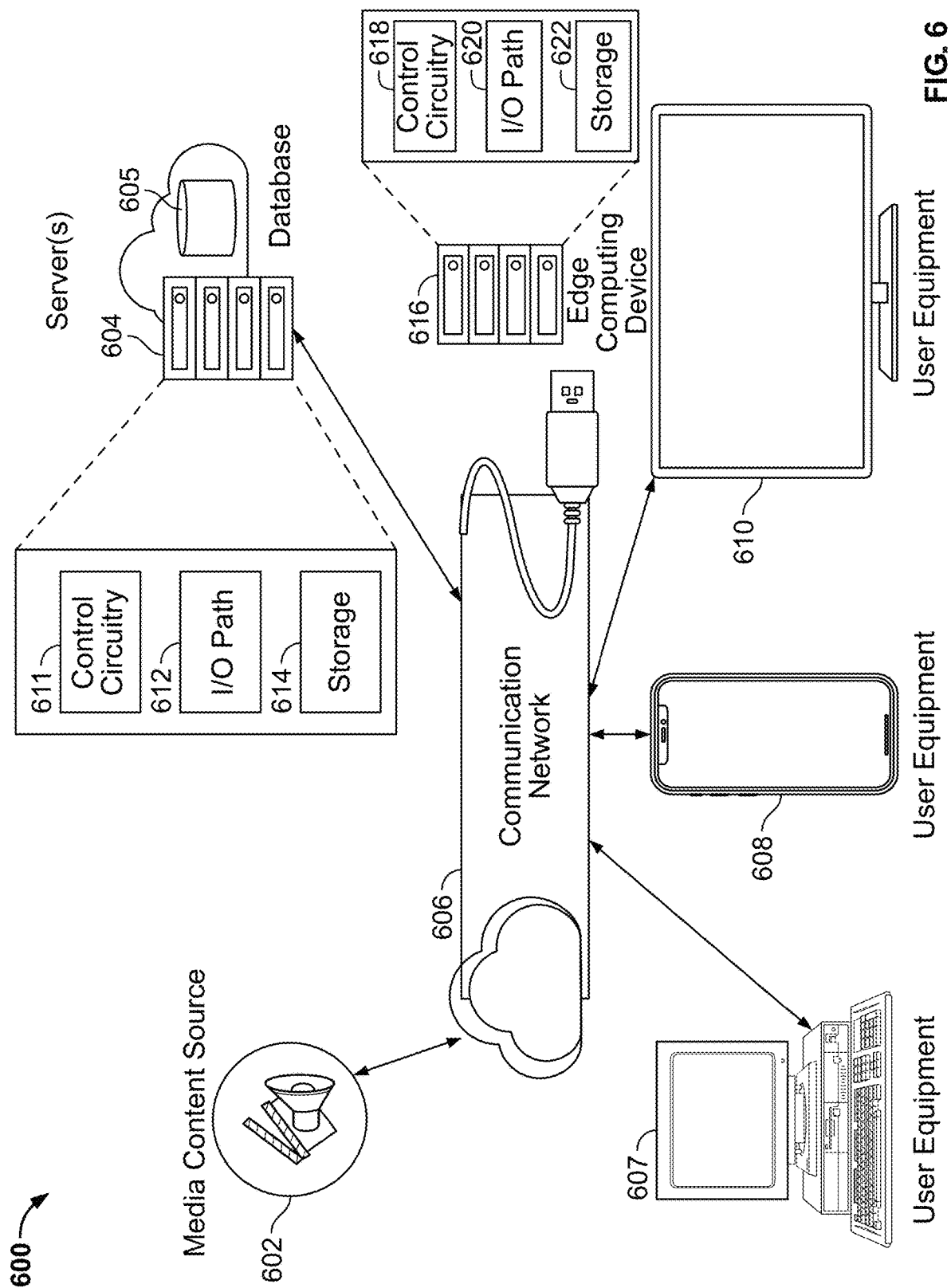
FIG. 6 shows an example system, in accordance with some embodiments of this disclosure.

FIGS. 5-6 depict illustrative devices, systems, servers, and related hardware for image feature detection. FIG. 5 shows generalized embodiments of illustrative user equipment devices 500 and 501, which may correspond to, e.g., computing devices 212, 260, 312, and 314. For example, user equipment device 500 may be a smartphone device, a tablet, a virtual reality or augmented reality device, or any other suitable device capable of processing video data. In another example, user equipment device 501 may be a user television equipment system or device. User television equipment device 501 may include set-top box 515. Set-top box 515 may be communicatively connected to microphone 516, audio output equipment (e.g., speaker or headphones 514), and display 512. In some embodiments, display 512 may be a television display or a computer display. In some embodiments, set-top box 515 may be communicatively connected to user input interface 510. In some embodiments, user input interface 510 may be a remote-control device. Set-top box 515 may include one or more circuit boards. In some embodiments, the circuit boards may include control circuitry, processing circuitry, and storage (e.g., RAM, ROM, hard disk, removable disk, etc.). In some embodiments, the circuit boards may include an input/output path.

Each one of user equipment device 500 and user equipment device 501 may receive content and data via input/output (I/O) path 502. I/O path 502 may provide content (e.g., broadcast programming, on-demand programming, Internet content, content available over a local area network (LAN) or wide area network (WAN), and/or other content) and data to control circuitry 504, which may comprise processing circuitry 506 and storage 508. Control circuitry 504 may be used to send and receive commands, requests, and other suitable data using I/O path 502, which may comprise I/O circuitry. I/O path 502 may connect control circuitry 504 (and specifically processing circuitry 506) to one or more communications paths (described below). I/O functions may be provided by one or more of these communications paths, but are shown as a single path in FIG. 5 to avoid overcomplicating the drawing. While set-top box 515 is shown in FIG. 6 for illustration, any suitable computing device having processing circuitry, control circuitry, and storage may be used in accordance with the present disclosure. For example, set-top box 515 may be replaced by, or complemented by, a personal computer (e.g., a notebook, a laptop, a desktop), a smartphone (e.g., device 600), a tablet, a network-based server hosting a user-accessible client device, a non-user-owned device, any other suitable device, or any combination thereof.

Control circuitry 504 may be based on any suitable control circuitry such as processing circuitry 506. As referred to herein, control circuitry should be understood to mean circuitry based on one or more microprocessors, microcontrollers, digital signal processors, programmable logic devices, field-programmable gate arrays (FPGAs), application-specific integrated circuits (ASICs), etc., and may include a multi-core processor (e.g., dual-core, quad-core, hexa-core, or any suitable number of cores) or supercomputer. In some embodiments, control circuitry may be distributed across multiple separate processors or processing units, for example, multiple of the same type of processing units (e.g., two Intel Core i7 processors) or multiple different processors (e.g., an Intel Core i5 processor and an Intel Core i7 processor). In some embodiments, control circuitry 504 executes instructions for the feature detection application stored in memory (e.g., storage 508). Specifically, control circuitry 504 may be instructed by the feature detection application to perform the functions discussed above and below. In some implementations, processing or actions performed by control circuitry 504 may be based on instructions received from the feature detection application.

In client/server-based embodiments, control circuitry 504 may include communications circuitry suitable for communicating with a server or other networks or servers. The feature detection application may be a stand-alone application implemented on a device or a server. The feature detection application may be implemented as software or a set of executable instructions. The instructions for performing any of the embodiments discussed herein of the feature detection application may be encoded on non-transitory computer-readable media (e.g., a hard drive, random-access memory on a DRAM integrated circuit, read-only memory on a BLU-RAY disk, etc.). For example, in FIG. 5, the instructions may be stored in storage 508, and executed by control circuitry 504 of a device 500.

In some embodiments, the feature detection application may be a client/server application where only the client application resides on device 500 (e.g., device 104), and a server application resides on an external server (e.g., server 604 and/or server 616). For example, the feature detection application may be implemented partially as a client application on control circuitry 504 of device 500 and partially on server 604 as a server application running on control circuitry 611. Server 604 may be a part of a local area network with one or more of devices 500 or may be part of a cloud computing environment accessed via the internet. In a cloud computing environment, various types of computing services for performing searches on the internet or informational databases, providing feature detection capabilities, providing storage (e.g., for a database) or parsing data (e.g., using machine learning algorithms described above and below) are provided by a collection of network-accessible computing and storage resources (e.g., server 604 and/or edge computing device 616), referred to as "the cloud." Device 600 may be a cloud client that relies on the cloud computing capabilities from server 604 to determine whether processing (e.g., at least a portion of virtual background processing and/or at least a portion of other processing tasks) should be offloaded from the mobile device, and facilitate such offloading. When executed by control circuitry of server 604 or 616, the feature detection application may instruct control 611 or 618 circuitry to perform processing tasks for the client device and facilitate the feature detection.

Control circuitry 504 may include communications circuitry suitable for communicating with a server, edge computing systems and devices, a table or database server, or other networks or servers. The instructions for carrying out the above mentioned functionality may be stored on a server (which is described in more detail in connection with FIG. 6). Communications circuitry may include a cable modem, an integrated services digital network (ISDN) modem, a digital subscriber line (DSL) modem, a telephone modem, Ethernet card, or a wireless modem for communications with other equipment, or any other suitable communications circuitry. Such communications may involve the Internet or any other suitable communication networks or paths (which is described in more detail in connection with FIG. 6). In addition, communications circuitry may include circuitry that enables peer-to-peer communication of user equipment devices, or communication of user equipment devices in locations remote from each other (described in more detail below).

Memory may be an electronic storage device provided as storage 508 that is part of control circuitry 504. As referred to herein, the phrase "electronic storage device" or "storage device" should be understood to mean any device for storing electronic data, computer software, or firmware, such as random-access memory, read-only memory, hard drives, optical drives, digital video disc (DVD) recorders, compact disc (CD) recorders, BLU-RAY disc (BD) recorders, BLU-RAY 3D disc recorders, digital video recorders (DVR, sometimes called a personal video recorder, or PVR), solid state devices, quantum storage devices, gaming consoles, gaming media, or any other suitable fixed or removable storage devices, and/or any combination of the same. Storage 508 may be used to store various types of content described herein as well as feature detection application data described above. Nonvolatile memory may also be used (e.g., to launch a boot-up routine and other instructions). Cloud-based storage, described in relation to FIG. 5, may be used to supplement storage 508 or instead of storage 508.

Control circuitry 504 may include video generating circuitry and tuning circuitry, such as one or more analog tuners, one or more MPEG-2 decoders or other digital decoding circuitry, high-definition tuners, or any other suitable tuning or video circuits or combinations of such circuits. Encoding circuitry (e.g., for converting over-the-air, analog, or digital signals to MPEG signals for storage) may also be provided. Control circuitry 504 may also include scaler circuitry for upconverting and downconverting content into the preferred output format of user equipment 500. Control circuitry 504 may also include digital-to-analog converter circuitry and analog-to-digital converter circuitry for converting between digital and analog signals. The tuning and encoding circuitry may be used by user equipment device 500, 501 to receive and to display, to play, or to record content. The tuning and encoding circuitry may also be used to receive video feature detection data. The circuitry described herein, including for example, the tuning, video generating, encoding, decoding, encrypting, decrypting, scaler, and analog/digital circuitry, may be implemented using software running on one or more general purpose or specialized processors. Multiple tuners may be provided to handle simultaneous tuning functions (e.g., watch and record functions, picture-in-picture (PIP) functions, multiple-tuner recording, etc.). If storage 508 is provided as a separate device from user equipment device 500, the tuning and encoding circuitry (including multiple tuners) may be associated with storage 508.

Control circuitry 504 may receive instruction from a user by way of user input interface 510. User input interface 510 may be any suitable user interface, such as a remote control, mouse, trackball, keypad, keyboard, touch screen, touchpad, stylus input, joystick, voice recognition interface, or other user input interfaces. Display 512 may be provided as a stand-alone device or integrated with other elements of each one of user equipment device 500 and user equipment device 501. For example, display 512 may be a touchscreen or touch-sensitive display. In such circumstances, user input interface 510 may be integrated with or combined with display 512. In some embodiments, user input interface 510 includes a remote-control device having one or more microphones, buttons, keypads, any other components configured to receive user input or combinations thereof. For example, user input interface 510 may include a handheld remote-control device having an alphanumeric keypad and option buttons. In a further example, user input interface 510 may include a handheld remote-control device having a microphone and control circuitry configured to receive and identify voice commands and transmit information to set-top box 515.

Audio output equipment 514 may be integrated with or combined with display 512. Display 512 may be one or more of a monitor, a television, a liquid crystal display (LCD) for a mobile device, amorphous silicon display, low-temperature polysilicon display, electronic ink display, electrophoretic display, active matrix display, electro-wetting display, electro-fluidic display, cathode ray tube display, light-emitting diode display, electroluminescent display, plasma display panel, high-performance addressing display, thin-film transistor display, organic light-emitting diode display, surface-conduction electron-emitter display (SED), laser television, carbon nanotubes, quantum dot display, interferometric modulator display, or any other suitable equipment for displaying visual images. A video card or graphics card may generate the output to the display 512. Audio output equipment 514 may be provided as integrated with other elements of each one of device 500 and equipment 501 or may be stand-alone units. An audio component of videos and other content displayed on display 512 may be played through speakers (or headphones) of audio output equipment 514. In some embodiments, audio may be distributed to a receiver (not shown), which processes and outputs the audio via speakers of audio output equipment 514. In some embodiments, for example, control circuitry 504 is configured to provide audio cues to a user, or other audio feedback to a user, using speakers of audio output equipment 514. There may be a separate microphone 516 or audio output equipment 514 may include a microphone configured to receive audio input such as voice commands or speech. For example, a user may speak letters or words that are received by the microphone and converted to text by control circuitry 504. In a further example, a user may voice commands that are received by a microphone and recognized by control circuitry 504. Camera 518 may be any suitable video camera integrated with the equipment or externally connected. Camera 518 may be a digital camera comprising a charge-coupled device (CCD) and/or a complementary metal-oxide semiconductor (CMOS) image sensor. In particular, Camera 518 may be a lensless CMOS sensor masked with a mask (e.g., as shown in FIG. 1 elements 102 and 104). Camera 518 may be an analog camera that converts to digital images via a video card.

The feature detection application may be implemented using any suitable architecture. For example, it may be a stand-alone application wholly-implemented on each one of user equipment device 500 and user equipment device 501. In such an approach, instructions of the application may be stored locally (e.g., in storage 508), and data for use by the application is downloaded on a periodic basis (e.g., from an out-of-band feed, from an Internet resource, or using another suitable approach). Control circuitry 504 may retrieve instructions of the application from storage 508 and process the instructions to provide feature detection functionality and preform any of the actions discussed herein. Based on the processed instructions, control circuitry 504 may determine what action to perform when input is received from user input interface 510. For example, movement of a cursor on a display up/down may be indicated by the processed instructions when user input interface 510 indicates that an up/down button was selected. An application and/or any instructions for performing any of the embodiments discussed herein may be encoded on computer-readable media. Computer-readable media includes any media capable of storing data. The computer-readable media may be non-transitory including, but not limited to, volatile and non-volatile computer memory or storage devices such as a hard disk, floppy disk, USB drive, DVD, CD, media card, register memory, processor cache, Random Access Memory (RAM), etc.

In some embodiments, the feature detection application is a client/server-based application. Data for use by a thick or thin client implemented on each one of user equipment device 500 and user equipment device 501 may be retrieved on-demand by issuing requests to a server remote to each one of user equipment device 500 and user equipment device 501. For example, the remote server may store the instructions for the application in a storage device. The remote server may process the stored instructions using circuitry (e.g., control circuitry 504) and generate the displays discussed above and below. The client device may receive the displays generated by the remote server and may display the content of the displays locally on device 500. This way, the processing of the instructions is performed remotely by the server while the resulting displays (e.g., that may include text, a keyboard, or other visuals) are provided locally on device 500. Device 500 may receive inputs from the user via input interface 510 and transmit those inputs to the remote server for processing and generating the corresponding displays. For example, device 500 may transmit a communication to the remote server indicating that an up/down button was selected via input interface 510. The remote server may process instructions in accordance with that input and generate a display of the application corresponding to the input (e.g., a display that moves a cursor up/down). The generated display is then transmitted to device 500 for presentation to the user.

In some embodiments, the feature detection application may be downloaded and interpreted or otherwise run by an interpreter or virtual machine (run by control circuitry 504). In some embodiments, the feature detection application may be encoded in the ETV Binary Interchange Format (EBIF), received by control circuitry 504 as part of a suitable feed, and interpreted by a user agent running on control circuitry 504. For example, the feature detection application may be an EBIF application. In some embodiments, the feature detection application may be defined by a series of JAVA-based files that are received and run by a local virtual machine or other suitable middleware executed by control circuitry 504. In some of such embodiments (e.g., those employing MPEG-2 or other digital media encoding schemes), feature detection application may be, for example, encoded and transmitted in an MPEG-2 object carousel with the MPEG audio and video packets of a program.

FIG. 6 is a diagram of an illustrative system 600 for feature detection, in accordance with some embodiments of this disclosure. User equipment devices 607, 608, 610 (e.g., which may correspond to one or more of computing device 212 may be coupled to communication network 606). Communication network 606 may be one or more networks including the Internet, a mobile phone network, mobile voice or data network (e.g., a 5G, 4G, or LTE network), cable network, public switched telephone network, or other types of communication network or combinations of communication networks. Paths (e.g., depicted as arrows connecting the respective devices to the communication network 606) may separately or together include one or more communications paths, such as a satellite path, a fiber-optic path, a cable path, a path that supports Internet communications (e.g., IPTV), free-space connections (e.g., for broadcast or other wireless signals), or any other suitable wired or wireless communications path or combination of such paths. Communications with the client devices may be provided by one or more of these communications paths but are shown as a single path in FIG. 6 to avoid overcomplicating the drawing.

Although communications paths are not drawn between user equipment devices, these devices may communicate directly with each other via communications paths as well as other short-range, point-to-point communications paths, such as USB cables, IEEE 1394 cables, wireless paths (e.g., Bluetooth, infrared, IEEE 702-11x, etc.), or other short-range communication via wired or wireless paths. The user equipment devices may also communicate with each other directly through an indirect path via communication network 606.

System 600 may comprise media content source 602, one or more servers 604, and one or more edge computing devices 616 (e.g., included as part of an edge computing system, such as, for example, managed by mobile operator 206). In some embodiments, the feature detection application may be executed at one or more of control circuitry 611 of server 604 (and/or control circuitry of user equipment devices 607, 608, 610 and/or control circuitry 618 of edge computing device 616). In some embodiments, data structure 300 of FIG. 3, may be stored at database 605 maintained at or otherwise associated with server 604, and/or at storage 622 and/or at storage of one or more of user equipment devices 607, 608, 610.

In some embodiments, server 604 may include control circuitry 611 and storage 614 (e.g., RAM, ROM, Hard Disk, Removable Disk, etc.). Storage 614 may store one or more databases. Server 604 may also include an input/output path 612. I/O path 612 may provide feature detection data, device information, or other data, over a local area network (LAN) or wide area network (WAN), and/or other content and data to control circuitry 611, which may include processing circuitry, and storage 614. Control circuitry 611 may be used to send and receive commands, requests, and other suitable data using I/O path 612, which may comprise I/O circuitry. I/O path 612 may connect control circuitry 611 (and specifically control circuitry) to one or more communications paths.

Control circuitry 611 may be based on any suitable control circuitry such as one or more microprocessors, microcontrollers, digital signal processors, programmable logic devices, field-programmable gate arrays (FPGAs), application-specific integrated circuits (ASICs), etc., and may include a multi-core processor (e.g., dual-core, quad-core, hexa-core, or any suitable number of cores) or supercomputer. In some embodiments, control circuitry 611 may be distributed across multiple separate processors or processing units, for example, multiple of the same type of processing units (e.g., two Intel Core i7 processors) or multiple different processors (e.g., an Intel Core i5 processor and an Intel Core i7 processor). In some embodiments, control circuitry 611 executes instructions for an emulation system application stored in memory (e.g., the storage 614). Memory may be an electronic storage device provided as storage 614 that is part of control circuitry 611.

Edge computing device 616 may comprise control circuitry 618, I/O path 620 and storage 622, which may be implemented in a similar manner as control circuitry 611, I/O path 612 and storage 624, respectively of server 604. Edge computing device 616 may be configured to be in communication with one or more of user equipment devices 607, 608, 610 and video server 604 over communication network 606, and may be configured to perform processing tasks (e.g., feature detection) in connection with ongoing processing of video data. In some embodiments, a plurality of edge computing devices 616 may be strategically located at various geographic locations, and may be mobile edge computing devices configured to provide processing support for mobile devices at various geographical regions.

Figure 7:
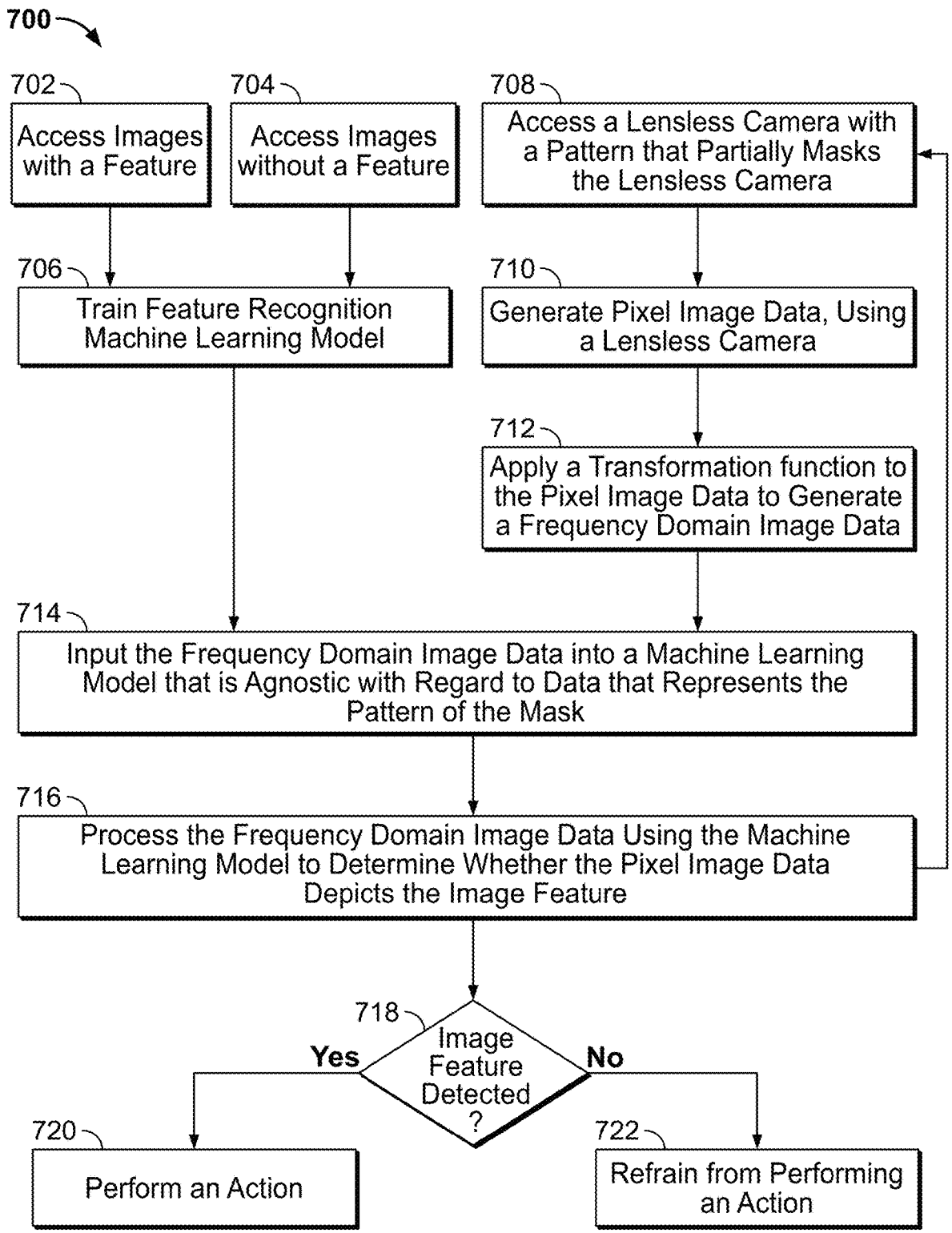
FIG. 7 is a flowchart of a detailed illustrative process for image feature detection, in accordance with some embodiments of this disclosure.

FIG. 7 is a flowchart of a detailed illustrative process 700 for feature detection, in accordance with some embodiments of this disclosure. In various embodiments, the individual steps of process 700 may be implemented by one or more components of the devices and systems of FIGS. 1-6. Although the present disclosure may describe certain steps of process 700 (and of other processes described herein) as being implemented by certain components of the devices and systems of FIGS. 1-6, this is for purposes of illustration only, and it should be understood that other components of the devices and systems of FIGS. 1-6 may implement those steps instead.

At training step 706, control circuitry (e.g., control circuitry 611, control circuitry 618, or control circuitry of any of devices 607, 608, or 610) may train a machine learning model (e.g., a model stored in storage 508). For example, the training step 706 may be performed during initial set up of computing device 500. For example, the machine learning model may be trained to recognize a face of a user (e.g., user 202) to enable computing device 500 to become unlocked in response to detection of the face of the user by camera 518 of computing device 500, such that the user may access full functionality of the computing device instead of limited functionality of the computing device that is executed only during the log-in phase (e.g., computing device in limited mode may only be able to perform basic start-up functions and feature detection functions to unlock the full functionality of the computing device, such as ability to run apps).

In particular, the training step 706 may be performed by the control circuitry based on accessing images 702 that are known to include the image feature (e.g., images with the face of the user). Optionally, the training step 706 may also be performed based on accessing images 704 that are known to not include the image feature (e.g., images without the face of the user and/or with faces of other users). For example, the control circuitry may access images 252 and 254 and train a machine learning model (e.g., model 401) as described in relation to FIG. 2B. In some embodiments, the accessed images at step 702 may have been images captured using the masked lensless camera (e.g., camera 518 of FIG. 5). For example, the user may be instructed (e.g., using a UI of user equipment 604, 608, or 610, such as a display 512) to stage a scene in front of the masked lensless camera to generate images known to include the image feature (for example, the UI output may instruct the user to face a camera from several angles if the image feature is presence of the user's face).

Once the machine learning model is trained, the control circuitry proceeds to step 708 to access a lensless camera (e.g., camera 518 of FIG. 5) that comprises a patterned mask that affects (e.g., modulates) light hitting the light-sensing element of the camera. In some embodiments, the lensless camera is the same camera with the same mask that was used to generate a training set of data for training the machine learning model. At step 710, the control circuitry may generate pixel image data (e.g., data 306 of FIG. 3) based on a signal processed by the lensless camera.

At step 712, the control circuitry applies a transformation function to the pixel image data to generate frequency domain image data (e.g., data 308). For example, the transformation function may be a discrete cosine transform, a Fourier transform, or a wavelet transform.

At step 714, the control circuitry inputs the frequency domain image data into the trained machine learning model (e.g., where the machine learning model does not have access to the data that defines the pattern of a mask that affects (e.g., modulates) light hitting the camera that was accessed in step 708). The trained machine learning model may have been trained at step 706. In some embodiments, the control circuitry does not have any kind of access to the data that defines the pattern of a mask, to preserve privacy. In some embodiments, the frequency domain image data may have been pre-processed before or after input into the trained machine learning model to separate it into several band sets (e.g., into bands 400-406 of FIG. 4) to be processed by several different pathways of the machine learning model (e.g., as shown in FIG. 4).

At step 716, the control circuitry, uses the trained machine learning model to process the frequency domain image data to determine whether the pixel image data (if it were un-distorted) would depict the same image feature that was included in all images received in step 702 that were used to train the machine learning model (e.g., whether a face of the user is present). Other example image features that may be detected by the control circuitry are further described in relation to FIG. 8.

At step 718, the control circuitry may follow multiple pathways depending on whether or not the image feature was detected. If the image feature was detected, the control circuitry, at step 720, performs a pre-defined function. For example, the control circuitry may unlock access to its full functionality if a face of a user was detected. Other example actions that may be performed by the control circuitry are further described in relation to FIG. 8. If the image feature was not detected, the control circuitry, at step 722, may return to step 708 and access the lensless camera to capture a new pixel image data to re-attempt detection of the feature. Optionally, or alternatively, at step 722, the control circuitry may also perform another function different from a function performed at step 720. For example, the control circuitry may display a failure notification on display 512. In other embodiments, the control circuitry may display a notification to adjust the input (e.g., asking the user to shift the angle of their face in relation to the capture device).

As a result, the control circuitry is able to detect an image feature (e.g., particular human face) by analyzing image pixel data captured by a flat, lensless camera distorted by a pattern without knowledge or access to data defining the pattern. This improves computer vision systems by allowing performance of actions normally taken in response to a feature detection, without allowing the control circuitry to create undistorted version of the image. Advantageously, even if an adverse computing system gains unauthorized access to the feed of the flat, lensless camera, that adverse computing system would be unable to reconstruct the image feature (e.g., depiction of the face of the user)—thus increasing security of the computing system. For example, if the system is unlocked based on face detection, the adverse computing system would not be able to construct an image of the face to gain unauthorized access to the system secured by face detection.

Figure 8:
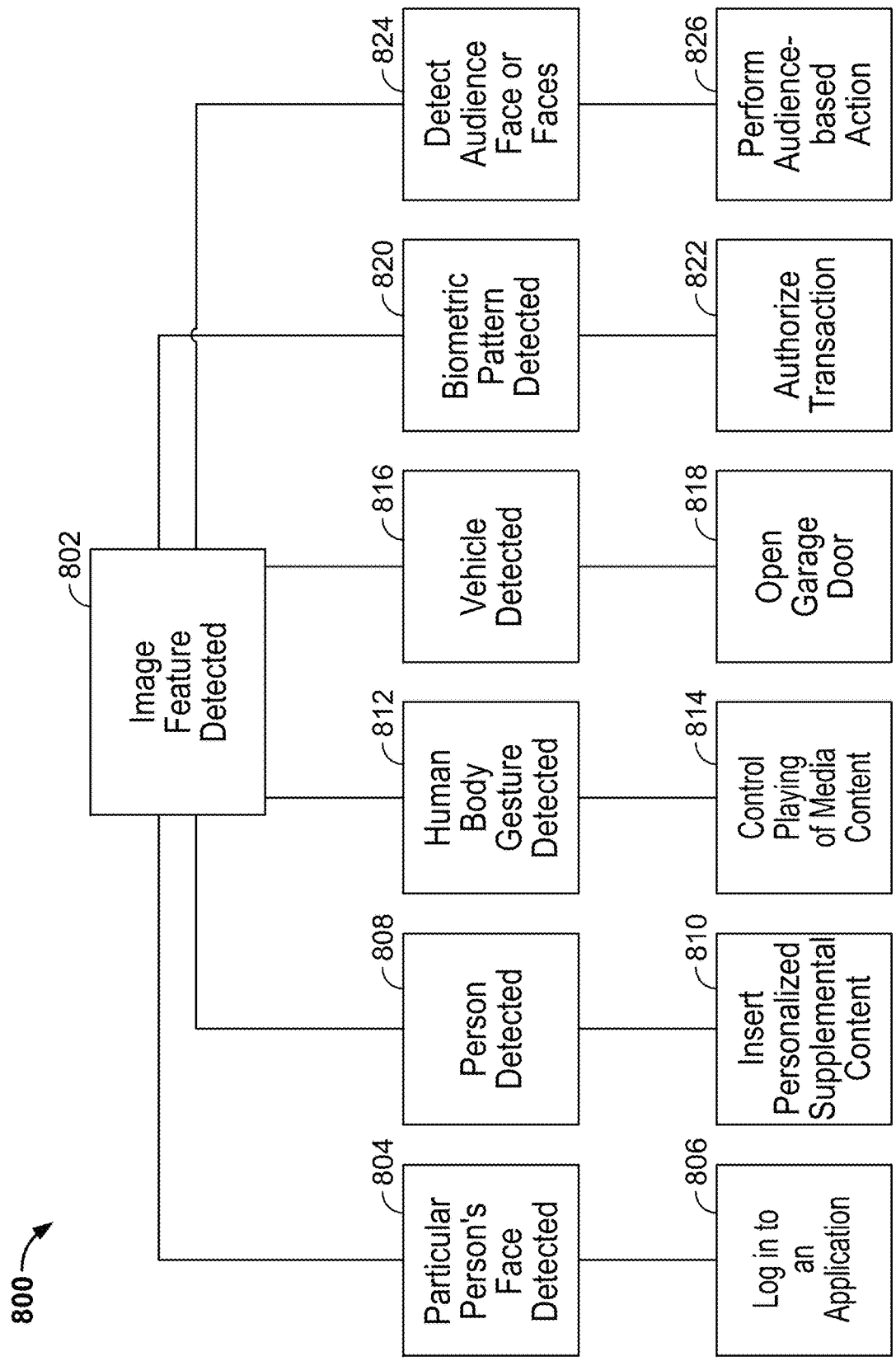
FIG. 8 is a flowchart of a detailed illustrative process for performing an action based on image feature detection, in accordance with some embodiments of this disclosure.

FIG. 8 is a flowchart of a detailed illustrative process 800 for performing an action based on image feature detection, in accordance with some embodiments of this disclosure. In various embodiments, the individual steps of process 700 may be implemented by one or more components of the devices and systems of FIGS. 1-6. Although the present disclosure may describe certain steps of process 700 (and of other processes described herein) as being implemented by certain components of the devices and systems of FIGS. 1-6, this is for purposes of illustration only, and it should be understood that other components of the devices and systems of FIGS. 1-6 may implement those steps instead. In some embodiments, steps 806, 810, 814, 818, and 822 may be performed as part of step 720 of FIG. 7.

At 802, control circuitry (e.g., control circuitry 611, control circuitry 618, or control circuitry of any of devices 607, 608, or 610) may detect a feature in a pixel image (e.g., in a pixel image captured by masked lensless camera 518). Such detection (e.g., using trained machine learning model 401) is described in further detail in steps 702-716 of FIG. 7. Depending on the type of feature that the trained machine learning model was trained to detect, the control circuitry may perform different actions.

For example, at step 804, the control circuitry may have detected presence of a particular face in the pixel image data. In this case, the control circuitry may, at step 806, log a user in to a particular application (e.g., into a media application designed to stream media assets). In some embodiments, in this implementation, the trained machine learning model is trained using images captured by the masked lensless camera known to include the particular face.

In another example, at step 808, the control circuitry may have detected presence of a particular person in the pixel image data. In this case, the control circuitry may, at step 810, insert personalized supplemental content that matches preferences in the user profile of the particular person. For example, the supplemental content may be inserted into media streamed by the media application to the user device. In one approach, the trained machine learning model may have been trained to recognize any of the members of the household. For example, the softmax function 462 may have been designed to compute the probability of the presence of any set of known users (e.g., using pictures taken by the masked lensless camera of every family member).

In another example, at step 812, the control circuitry may have detected presence of a particular human body gesture in the pixel image data (e.g., waving or raising hands to the sides). In this case, the control circuitry may, at step 814, control playing of the media content (e.g., by the media application) based on the gesture. For example, the media streamed by the media application to the user device may be paused when a wave is detected. In another example, the media streamed by the media application to the user device may be streamed with increased volume when hands being raised to the sides are detected. In one approach, the trained machine learning mode may have been trained to recognize any set of gestures. For example, the softmax function 462 may have been designed to compute the probability of the presence of any of a set of known gestures (e.g., using pictures taken by the masked lensless camera of every gesture).

In another example, at step 816, the control circuitry may have detected presence of a particular vehicle in the pixel image data. In this case, the control circuitry may, at step 818, open garage door based on the gesture. In some embodiments, in this implementation, the trained machine learning mode is trained using images captured by the masked lensless camera known to include the particular vehicle.

In another example, at step 820, the control circuitry may have detected presence of a particular biometric pattern (e.g., fingerprint or iris pattern). In this case, the control circuitry may, at step 822, authorize a transaction based on the biometric pattern. In some embodiments, in this implementation, the trained machine learning model is trained using images captured by the masked lensless camera known to include the particular biometric pattern. For example, the control circuitry may be a part of an automated teller machine and may authorize dispensing of bank notes using the biometric pattern detection.

In another example, at step 824, the control circuitry may have detected presence of one or more particular faces in the pixel image data. In this case, the control circuitry may, at step 826, perform an audience-based action, e.g., perform updates to viewing history for each identified user (for example for use in customizing future media presentation to each user or for providing supplemental media content to each user based on their respective veiwing history). In such an example, a television or media set-top box may capture distorted images (e.g., by using the masked camera) of one or more family members and identify viewers to be used for, e.g., audience statistics, viewer preferences, viewer profiles, targeted advertising, etc., without concerns of visible photographs being captured within the home and potentially seen by unknown members of the public. In some embodiments, in this implementation, the trained machine learning model is trained using images captured by the masked lensless camera known to include a particular face.

Figure 9B:
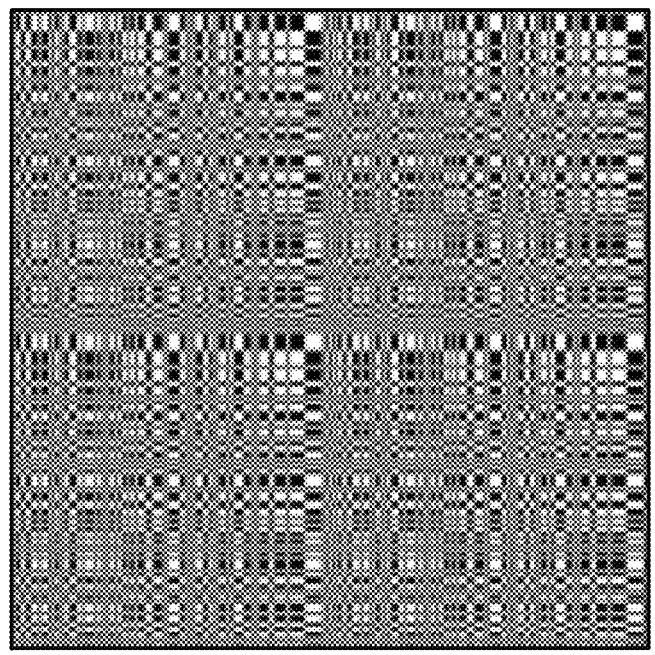
FIG. 9B shows a view of another example mask, in accordance with some embodiments of this disclosure.
Figure 9A:
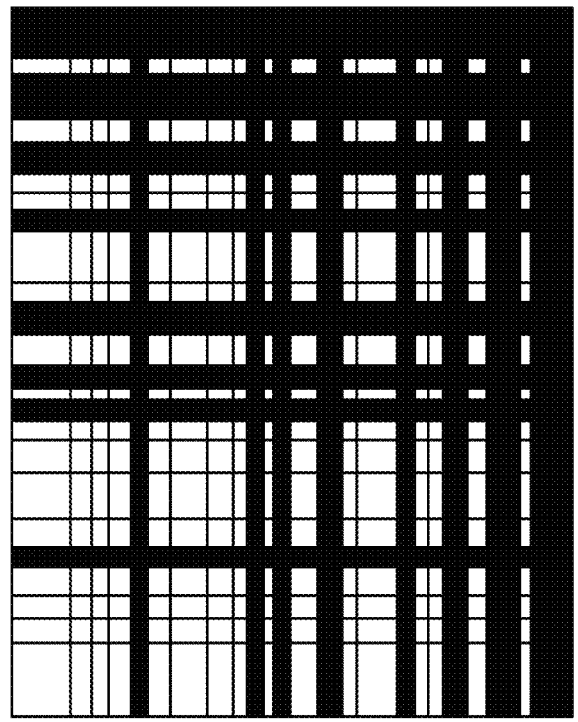
FIG. 9A shows a view of an example mask, in accordance with some embodiments of this disclosure.

FIGS. 9A and 9B show views of additional example masks 900 and 950, with patterns (e.g., randomly generated patterns) that may be used to mask a lensless camera (e.g., lensless camera 518 of FIG. 5). For example, the mask may be manufactured using any suitable opaque material. In some embodiments, masks 900 and 950 may also be placed at a variable distance away from the light-sensing portion of the lensless camera to further complicate reconstruction of un-distorted pixel data. For example, the distance may be randomly set by the manufacturer or adjusted manually by the end user.

The processes discussed above are intended to be illustrative and not limiting. One skilled in the art would appreciate that the steps of the processes discussed herein may be omitted, modified, combined and/or rearranged, and any additional steps may be performed without departing from the scope of the invention. More generally, the above disclosure is meant to be illustrative and not limiting. Only the claims that follow are meant to set bounds as to what the present invention includes. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

What is claimed is:

1. A method comprising:

generating pixel image data, using a lensless camera, based on light that travels to the lensless camera through a mask that comprises a pattern for masking the lensless camera;

applying a transformation function to the pixel image data to generate frequency domain image data;

processing the frequency domain image data using a machine learning model to determine whether the pixel image data depicts an image feature at least by:

inputting the frequency domain image data into the machine learning model, wherein the machine learning model does not have access to data that represents the pattern of the mask, wherein the machine learning model is trained using a set of one or more images captured by the lensless camera through the mask that are known to depict the image feature;

and performing an action based on determining that the pixel image data depicts the image feature.

2. A method of claim 1, wherein the processing of the frequency domain image data using the machine learning model comprises:

dividing the frequency domain image data into a plurality of bands;

inputting each band of the plurality of bands into a convolution layer of the machine learning model;

generating an attention map for each band;

concatenating the attention map generated for each band;

inputting the concatenated attention maps into another convolution layer of the machine learning model;

generating an additional attention map for the concatenated attention maps;

inputting the additional attention map into at least one fully connected layer of the machine learning model; and generating a probability of the pixel image data depicting the image feature based on the output of the at least one fully connected layer of the machine learning model.

3. A method of claim 2, wherein the transformation function is a discrete cosine transform function.

4. A method of claim 3, wherein the plurality of bands comprises:

a first band comprising a direct current (DC) component and low-frequency alternating current (AC) components of the frequency domain image data;

a second band comprising a horizontal frequency portion of the frequency domain image data;

a third band comprising a vertical frequency portion of the frequency domain image data; and a fourth band comprising a high-frequency diagonal portion of the frequency domain image data.

5. A method of claim 2, wherein generating the probability of the pixel image data depicting the image feature comprises applying a softmax function to the output of the at least one fully connected layer of the machine learning model.

6. A method of claim 2, wherein the inputting each band of the plurality of bands into a convolution layer of the machine learning model and wherein the generating the attention map for each band results in reduction of dimensionality of the inputted bands.

7. A method of claim 1, wherein the image feature comprises presence of a face of a particular human in the image.

8. A method of claim 7, wherein the performing the action based on the determining that the pixel image data depicts the image feature comprises:

receiving a request to authenticate a transaction requested by a user; and authenticating the transaction based on determining that the pixel image data depicts a face of the user to permit the transaction to occur.

9. A method of claim 7, wherein the performing the action based on the determining that the pixel image data depicts the image feature comprises:
receiving a request to log in to an application using an account of a user;
logging in to an application based on determining that the pixel image data depicts a face of the user.

10. A method of claim 1, wherein the mask comprises:
opaque material in the shape of the pattern; and
apertures that permit passage of light in portions of the mask outside of the pattern.

11. A method of claim 10, wherein the pattern of the mask is randomly generated.

12. A system comprising:
a lensless camera that is configured to:
generate pixel image data based on light that travels to the lensless camera through a mask that comprises a pattern for masking the lensless camera; and
control circuitry configured to:
apply a transformation function to the pixel image data to generate frequency domain image data;
process the frequency domain image data using a machine learning model to determine whether the pixel image data depicts an image feature at least by:
inputting the frequency domain image data into the machine learning model, wherein the machine learning model does not have access to data that represents the pattern of the mask, wherein the machine learning model is trained using a set of one or more images captured by the lensless camera through the mask that are known to depict the image feature;
and perform an action based on determining that the pixel image data depicts the image feature.

13. A system of claim 12, wherein the control circuitry is configured to process the frequency domain image data using the machine learning model, by:
dividing the frequency domain image data into a plurality of bands;
inputting each band of the plurality of bands into a convolution layer of the machine learning model;
generating an attention map for each band;
concatenating the attention maps generated for each band;
inputting the concatenated attention maps into another convolution layer of the machine learning model;
generating an additional attention map for the concatenated attention maps;
inputting the additional attention map into at least one fully connected layer of the machine learning model; and
generating a probability of the pixel image data depicting the image feature based on the output of the at least one fully connected layer of the machine learning model.

14. A system of claim 13, wherein the transformation function is a discrete cosine transform function.

15. A system of claim 14, wherein the plurality of bands comprises:
a first band comprising direct current (DC) component and low frequency alternating current (AC) components of the frequency domain image data;
a second band comprising horizontal frequency portion of the frequency domain image data;
a third band comprising vertical frequency portion of the frequency domain image data; and
a fourth band comprising high frequency diagonal portion of the frequency domain image data.

16. A system of claim 13, wherein the control circuitry is configured to generate the probability of the pixel image data depicting the image feature by applying a softmax function to the output of the at least one fully connected layer of the machine learning model.

17. A system of claim 13, wherein the control circuitry is configured to input each band of the plurality of bands into a convolution layer of the machine learning model, and wherein the generating the attention map for each band results in reduction of dimensionality of the inputted bands.

18. A system of claim 12, wherein the image feature comprises presence of a face of a particular human in the image.

19. A system of claim 18, wherein the control circuitry is configured to perform the action based on the determining that the pixel image data depicts the image feature by:
receiving a request to authenticate a transaction requested by a user; and
authenticating the transaction based on determining that the pixel image data depicts a face of the user to permit the transaction to occur.

20. A system of claim 18, wherein the control circuitry is configured to perform the action based on the determining that the pixel image data depicts the image feature by:
receiving a request to log in to an application using an account of a user;
logging in to an application based on determining that the pixel image data depicts a face of the user.

* * * * *